(12) United States Patent
Royer

(10) Patent No.: US 10,583,268 B2
(45) Date of Patent: Mar. 10, 2020

(54) USE OF THE MODULATION OF A SIGNAL BY A SKIN CONTACT IMPEDANCE FOR THE MAINTENANCE AND DEVELOPMENT OF PHYSICAL OR MENTAL ABILITIES

(71) Applicant: Philippe Royer, Paris (FR)

(72) Inventor: Philippe Royer, Paris (FR)

( * ) Notice: Subject to any disclaimer, the term of this patent is extended or adjusted under 35 U.S.C. 154(b) by 0 days.

(21) Appl. No.: 16/072,513

(22) PCT Filed: Jan. 26, 2017

(86) PCT No.: PCT/FR2017/050181
§ 371 (c)(1),
(2) Date: Jul. 25, 2018

(87) PCT Pub. No.: WO2017/129909
PCT Pub. Date: Aug. 3, 2017

(65) Prior Publication Data
US 2019/0046759 A1     Feb. 14, 2019

(30) Foreign Application Priority Data
Jan. 26, 2016   (FR) ..................................... 16 50603

(51) Int. Cl.
*A61M 21/02*     (2006.01)
*A61B 5/053*     (2006.01)
(Continued)

(52) U.S. Cl.
CPC ........... *A61M 21/02* (2013.01); *A61B 5/0531* (2013.01); *A61F 4/00* (2013.01); *A61M 21/00* (2013.01); *G06F 3/015* (2013.01); *H03K 17/9645* (2013.01); *H03K 17/9647* (2013.01); *A61M 2021/0027* (2013.01); *A61M 2021/0044* (2013.01); *A61M 2205/13* (2013.01); *A61M 2205/3569* (2013.01);
(Continued)

(58) Field of Classification Search
CPC .... G08C 17/02; G08C 19/28; G08C 2201/20; G08C 2201/92; G08C 23/04; G08C 2201/21; G08C 17/00; G08C 2201/30; G08C 2201/40
USPC ........................................................ 340/12.23
See application file for complete search history.

(56) References Cited

U.S. PATENT DOCUMENTS

2011/0306303 A1* 12/2011 Choi ........................ G06F 3/011
455/66.1
2013/0211277 A1* 8/2013 Berg ................. A61M 21/0094
600/547

* cited by examiner

*Primary Examiner* — Mark S Blouin
(74) *Attorney, Agent, or Firm* — PatShegen IP LLC; Moshe Pinchas

(57) ABSTRACT

The invention relates to the use of the modulation of an audio and/or visual signal by a variation in the impedance of at least one contact with the skin of at least one user, for the maintenance and/or development of the user's physical and/or mental abilities.
The invention comprises the use of a device (100) for controlling the delivery of a medium, said device comprising:
 a first skin electrode (105) configured to generate electric waves, positioned against the skin of a first user;
 a second skin electrode (110) configured to capture electric waves, positioned against the skin of a second user, where the second user can be the first user;
 a detector (115) for detecting the value of an impedance parameter of the junction connecting the electrodes and passing through the contact with the skin of each user; and
 a control means (120) configured to transmit a medium-delivery command according to the value detected.

15 Claims, 5 Drawing Sheets

(51) Int. Cl.
*A61F 4/00* (2006.01)
*H03K 17/96* (2006.01)
*G06F 3/01* (2006.01)
*A61M 21/00* (2006.01)

(52) U.S. Cl.
CPC ............... *A61M 2205/3592* (2013.01); *A61M 2205/505* (2013.01); *A61M 2205/59* (2013.01); *A61M 2209/088* (2013.01); *A61M 2230/06* (2013.01); *A61M 2230/65* (2013.01); *H03K 2217/94089* (2013.01)

USE OF THE MODULATION OF A SIGNAL BY A SKIN CONTACT IMPEDANCE FOR THE MAINTENANCE AND DEVELOPMENT OF PHYSICAL OR MENTAL ABILITIES

TECHNICAL FIELD OF THE INVENTION

The present invention relates to a use of the modulation of a signal by a skin contact impedance for the maintenance and development of the user's physical and/or mental abilities and, more specifically, a use of the modulation of an audio and/or visual signal by a variation in the skin contact impedance of at least one user to maintain and/or develop the user's physical and/or mental abilities. It applies, in particular, to medical support of patients in a state of isolation.

STATE OF THE ART

People in a state of precarity can suffer physical, mental, sensory and social isolation. To break this isolation, specialized staff support these people through exercises aimed at exercising creativity and the ability to communicate.

Current exercises aim to boost synesthesia, ie the association of one sense to another.

However, no current system enables a single person to exercise his creativity in controlling a medium using only his sense of touch and without activating a man-machine interface, such as a touchscreen for example.

In addition, none of these current systems make it possible to compensate for a handicap or amplify the cerebral mobilization of patients.

Devices described in documents WO 2005/121939, US 2012/0262369, US 2015/0177891, US 2011/0134074, US 2011/0306303 and US 2013/0002544, are known. These devices are remote controls for controlling a computer or electronic device with sensors positioned on a user's skin. They in no way make it possible to maintain or develop physical or mental abilities, and even less to place at least two people in an electrical relationship for this purpose.

SUBJECT OF THE INVENTION

The present invention aims to remedy all or part of these drawbacks. To this end, the present invention relates to a use of the modulation of an audio and/or visual signal by a variation in the impedance of at least one contact with the skin of at least one user, for the maintenance and/or development of the user's physical and/or mental abilities, utilizing a device for controlling the delivery of a medium, said device comprising:
- a first skin electrode configured to generate electric waves, positioned against the skin of a first user;
- a second skin electrode configured to capture electric waves, positioned against the skin of a second user, where the second user can be the first user;
- a detector for detecting the value of an impedance parameter of the junction connecting the electrodes and passing through the contact with the skin of each user; and
- a control means configured to emit a medium-delivery command according to the value detected.

Thanks to these provisions, it is possible to generate a synesthesia phenomenon for each user, associating touch to another sense, such as hearing or sight, for example. The most reactive areas of the body are those where the mechanoreceptors are most numerous, ie hands and feet for example. This bodily geography makes it possible to vary the pressure, the connection surface and the contact areas to generate data. The connection duration increases the heat and, therefore, the value of the parameter measured. The impedance is also changed by humidification or insulation.

These provisions therefore make it possible to create links to respond to the physical, mental, sensory and social isolation of people in a state of precarity:
- for people with aphasia, these provisions make it possible to communicate;
- for people who are physically handicapped or have multiple handicaps, these provisions act as a creation tool, indicator of abilities, through contact with the smallest piece of skin;
- for elderly people, these provisions make it possible to mobilize conscious and unconscious memory through the medium played and touch;
- for all people with reduced mobility, these provisions enable the movement of the body, simulation of the mechanoreceptors; and
- for any other type of user, these provisions enable a somatic practice, which brings relaxation by focusing the senses.

Specialized staff supporting people in a state of precarity, who can suffer from physical, mental, sensory and social isolation, can, by utilizing this invention, break this isolation through exercises aimed at exercising creativity and the ability to communicate. In addition, the user patient can regain and control the sensation of his body, in particular his sense of touch.

In some embodiments, at least one contact for which impedance is detected is a contact between two different users.

In this way, specialist staff can take part in exercises performed by patients.

In some embodiments, the modulation of an audio and/or visual signal comprises the modulation of the frequency of said signal. For example, the sound frequency of a sound or a sonic work is increased when the impedance of the contact decreases. For example, the wavelengths emitted by a light source decrease with the impedance of the contact. These variations make the variation effect of the skin contact perceptible.

In some embodiments, the modulation of an audio and/or visual signal comprises the modulation of the rhythm of said signal. For example, the rhythm of a regular beat or the playback rhythm of a sonic work depends on the impedance of the skin contact.

In some embodiments, the impedance parameter detected is the resistivity of the junction.

In some embodiments, the control means is separate from the detector and electrodes, the device comprising a means for transmitting a wireless signal representative of the value detected towards the control means.

These embodiments make it possible for the user or users not to be restricted in their movements because of transmission cables connecting them to the control means.

In some embodiments, the device comprises an independent source of electrical power, configured to supply the first electrode with electrical current.

These embodiments make it possible for the user not to be restricted in his movements because of power cables connecting him to the control means.

In some embodiments, the device comprises a bracelet comprising the first electrode.

These embodiments make it possible to hide the electrode from view and give this electrode a more attractive appearance.

In some embodiments, the device comprises a plurality of first and/or second electrodes.

These embodiments make it possible to homogenize the capture or generation of waves in the skin.

In some embodiments, the control means controls the emission of a sound signal for which an emission parameter is determined as a function of the value detected.

These embodiments make it possible to associate the sense of hearing to the sense of touch.

In some embodiments, the control means controls the emission of a light signal for which an emission parameter is determined as a function of the value detected.

These embodiments make it possible to associate the sense of sight to the sense of touch.

In some embodiments, the control means controls the emission of a trigger signal in an audiovisual medium being played.

These embodiments make it possible to control an action in an interactive medium, such as a video game for example, the device thus acting as a man-machine interface.

In some embodiments, the control means controls the emission of a modulation signal for a medium being played.

These embodiments make it possible to modulate a medium known to the user as a function of contacts between skins.

In some embodiments, at least one electrode is carried by a panel on which the user places at least one part of his body. These embodiments make it possible to not place electrodes on the skin of the user, who can merely move or balance his feet or body on the panels to benefit from the effects of this invention.

In some embodiments, the modulation of an audio and/or visual signal also depends on physiological data of at least one user, captured by the device, the device comprising at least one sensor of a user's physiological data. In some embodiments, at least one item of physiological data is a heart rate. In this way the user's feeling of his body and emotions is enhanced.

BRIEF DESCRIPTION OF THE FIGURES

Other advantages, aims and particular features of the invention will become apparent from the non-limiting description that follows of at least one particular embodiment of devices and methods for the use that is the subject of the present invention, with reference to drawings included in an appendix, wherein.

DESCRIPTION OF EXAMPLES OF REALIZATION OF THE INVENTION

Figure 1:
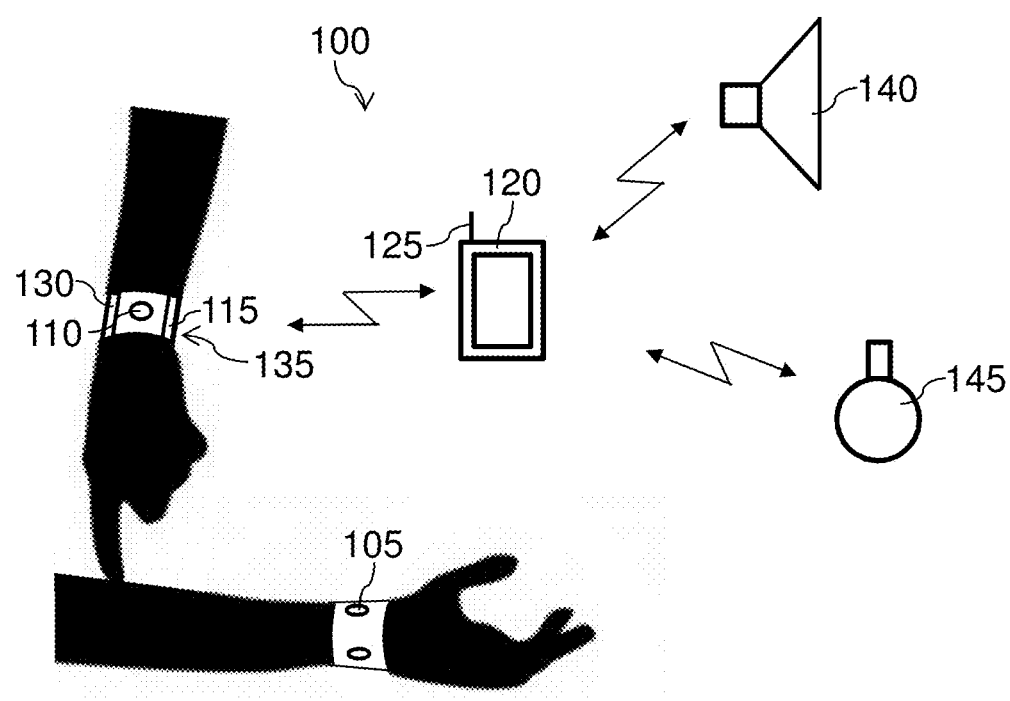
FIGS. 1 and 2 represent, schematically, particular embodiments of devices for the utilization of the present invention.

The present description is given in a non-limiting way, each characteristic of an embodiment being able to be combined with any other characteristic of any other embodiment in an advantageous way.

It is now noted that the figures are not to scale.

The term "communicating portable terminal" refers to any device equipped with:
 a man-machine interface; and
 a means for communicating wired or wireless signals, such as an antenna or a port to receive a network cable, for example.

Such a communicating portable terminal is, for example:
 a smartphone;
 a digital tablet; or
 a personal computer.

Before describing the devices making possible the utilization of the present invention, details are given below about the various embodiments of the use of the so modulation of an audio and/or visual signal by a variation in the impedance of at least one contact with the skin of at least one user, for the maintenance and/or development of the user's physical and/or mental abilities.

Preferably, this use uses a continuous flow of data representative of skin contact, possibly according to several parameters:
 the area of contact with more or fewer sensory sensors;
 the surface of contact (number of fingers, surface of the foot arch or back) etc;
 the pressure exerted on this contact;
 the temperature, a cold body having a lower electrical resistance than a warm body;
 the impedance, especially in the case of a tissue more or less insulating (for example according to its humidity);

Continuous verification of the impedance of the skin contact enables the use according to the invention to be practiced, since it is the exploration of the difference of values, associated to the generation of sounds or lights, which enables and triggers the involvement of the user(s).

The practice of synesthesia, a link between the senses (touch, hearing or sight), triggers the involvement of the physical body (somatic), thanks to mental feedback (psyche), through music or visual spectacle. Like a veritable musical instrument or instrument creating visual effects, the value detected generates the timbre, pitch, wavelength, intensity and rhythm. The gesture varying the impedance is deductive since it is hearing the sound production or seeing light effects that determines the gesture to be employed.

The application is therefore intimately linked since it makes possible the richness of real-time interactive feedback: frequencies, envelopes, volumes, combined by trigger threshold parameters, and interacting by combining or distributing digital audio files: managing the volume and pitch of ambient sounds (water, sea, birds), pre-existing music.

The invention therefore provides a tool for augmented communication and a solution to a specific communication problem of handicapped people. It enables a paralyzed person to be a player with the smallest piece of skin, an autistic person or aphasic person to communicate.

The user, in addition to entertainment, focuses his senses as in any somatic practice (yoga, full consciousness, etc) with, in addition, a relaxing effect.

The invention also provides a physical therapy tool, by physical mobilization. For example, when the electrodes are on the ground (for example, in the form of plates), differences in foot pressure are audible as differences in sound pitch; thus, proprioception is worked on.

The invention also provides a physical therapy tool, using mental mobilization: the skin is certainly a sensory sensor, but also a system for social connection, not to forget sexuality. The music and soundscapes proposed (water, wind, sea, children's laughter, etc) mobilize the memory.

In this way, the invention makes it possible to improve physical and cognitive abilities, and could be made available to people suffering from psychiatric disorders (depression, burn-out), and also to elderly people as a preventive tool.

The invention also provides a tool at the service of professional and family caregivers.

FIG. 1, which is not to scale, shows a schematic view of an embodiment of a device 100 for the utilization of the present invention. This device 100 for controlling the delivery of a medium comprises:

a first skin electrode 105 configured to generate electric waves, positioned against the skin of a first user;

a second skin electrode 110 configured to capture electric waves, positioned against the skin of a second user, where the second user can be the first user;

a detector 115 for detecting the value of an impedance parameter of the junction connecting the electrodes and passing through the contact with the skin of each user; and a control means 120 configured to emit a medium-delivery command according to the value detected.

The first electrode 105 comprises, or is connected to, an oscillator type of electric wave generator. This oscillator is, preferably, of harmonic type, ie configured to produce a sinusoidal waveform. This oscillator is, for example:

Colpitts oscillator;
Clapp oscillator;
phase-shift oscillator;
Pierce oscillator;
Hartley oscillator; or
state-variable oscillator.

The electrical current communicated to the skin of the first user has, for example, an intensity of 1.5 milliamperes and a voltage of 9 Volts. The diameter of this first electrode 105 is, for example, less than two centimeters.

This first electrode 105 is connected to a means for controlling the device 100 configured to activate or deactivate the wave generator. This control means is, for example, a push-button or a communicating portable terminal transmitting a wireless signal activating or deactivating the wave generator.

This first electrode 105 is placed on a panel of large size relative to the dimensions of the electrode 105. The term "large size" refers to a surface at least five times greater than the surface of the first electrode 105.

In some preferred embodiments, such as that shown in FIG. 1, the device 100 comprises a plurality of first electrodes 105.

The advantages of using multi-electrode systems are:
the generation of independent delivery commands for the same or different media, thus enhancing the media range, sound signal and/or light signal and/or audiovisual medium and/or interactive medium; and
the ability to use the device 100 alone or with others.

The electrodes, 105 and 110, and the detector 115 can be positioned on large panels, which enables a polyphonic or multimedia use by the movement of the feet or body on this assembly of panels, separate or not.

In some variants, at least one electrode is positioned against a surface separate from the user of the system. This surface is, for example, a floor or a wall. The advantage of such positioning is that no bracelet need be worn, as it is very difficult or impossible to place on users with autism spectrum disorders. In this way, the contact of the foot, walking, or of any part of the body, completes the connection between the electrodes. Moving from panel to panel, alone or with others, enables a medium-delivery command to be generated.

Where the device 100 comprises several first electrodes 105, each first electrode 105 can be communicative separately from each other first electrode 105. In some variants, a single first electrode 105 is communicative, along a wired or wireless connection, with a remote device, and every other first electrode 105 is connected to the communicating first electrode 105.

In some preferred embodiments, such as that shown in FIG. 1, the device 100 comprises a bracelet 135 comprising each first electrode 105.

This bracelet 135 is worn, for example, on the wrist of the first user.

The second electrode 110 comprises, or is connected to, an electric wave sensor.

This second electrode 110 is placed on a panel of large size relative to the dimensions of the electrode 110. The term "large size" refers to a surface at least five times greater than the surface of the second electrode 110.

In some preferred embodiments (not shown), the device 100 comprises a plurality of second electrodes 110.

Where the device 100 comprises several second electrodes 110, each second electrode 110 can be communicative separately from each other second electrode 110. In some variants, a single second electrode 110 is communicative, along a wired or wireless connection, with a remote device, and every other second electrode 110 is connected to the communicating second electrode 110.

In some preferred embodiments, such as that shown in FIG. 1, the device 100 comprises a bracelet (not referenced) comprising each second electrode 110.

This bracelet 135 is worn, for example, on the wrist of the second user.

In this way, when the first user and the second user are in contact, the waves generated by the first electrode 105 are captured by the second electrode 110.

In a particular embodiment, the first electrode 105 and the second electrode 110 are worn by a single user, and the contact of a first part of the body with a second part of the body changes the path the waves take in the body.

In the absence of contact, when each electrode, 105 and 110, is positioned on a different wrist of the user, the waves are transmitted through the arms and torso of the user.

As soon as the user, with one of his hands, touches the other forearm, the path traversed by the waves becomes: a part of one arm, hand, then another part of an arm, to the sensor; this path being shorter than the path when there is no contact.

Figure 2:
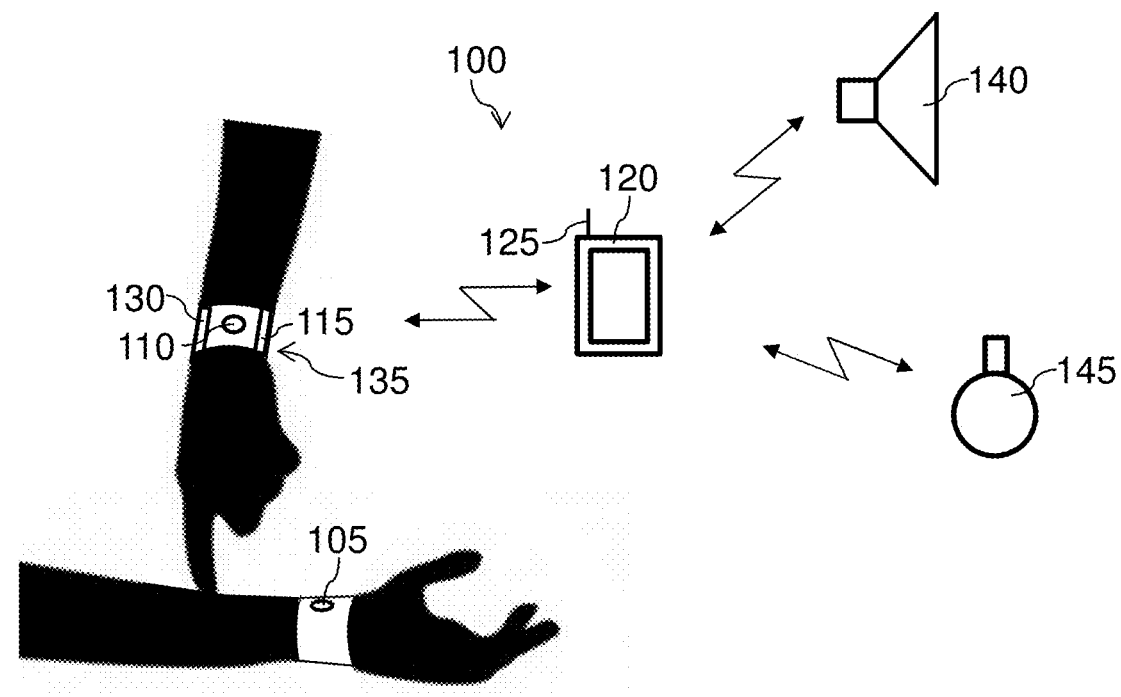

FIGS. 1 and 2 show two different positions of the contact between the users, these positions resulting in different impedance parameter values.

The detector 115 is, for example, an electric circuit configured to compare the electric wave emitted and the electric wave captured to determine, for example, the:
- resistivity,
- conductivity,
- resistance,
- impedance, and/or
- capacitance of the junction connecting the first and the second electrode, 105 and 110, and passing by contact with the skin of each user.

In this way, each of these parameters changes as a function of the position of the contact between the users, the pressure exerted at the location of this contact, and the surface of this contact.

The detected parameter value is transmitted to the control means 120.

The control detector 115 is positioned:
- either near the electrodes, to be carried by the user, and transporting the sound by HF transmission;
- or at the location of a communicating portable terminal with a wired connection to the electrodes, 105 and 110.

The control means 120 is, for example, an electronic circuit incorporated in a communicating terminal, this electronic circuit emitting commands to:
- an electroacoustic transducer 140;
- an emitter 145 of light signals; and/or
- a peripheral to play an audiovisual medium.

This control means 120 preferably comprises a computer program controlling the electronic circuit, this computer program being configured to:
- acquire the signal captured by the detector 115 via the second electrode 110;
- normalize and smooth this signal;
- remaster this normalized and smoothed signal;
- determine:
    - event trigger thresholds;
    - continuous verifications on some synthesis parameters:
        - by sampling;
        - by frequency modulation;
        - by additive synthesis; and
- mix the signal to be played.

This control means 120 emits a command that depends on the transmitted parameter value.

For example, the control means 120 emits a command to emit a sound at a frequency whose value is determined as a function of the transmitted parameter value. For example, the higher the detected resistivity, the higher the emission frequency or amplitude of a sound signal. This sound can be polyphonic.

In some embodiments, the control means 120 controls the emission of a sound signal for which an emission parameter is determined as a function of the value detected.

Figure 3:
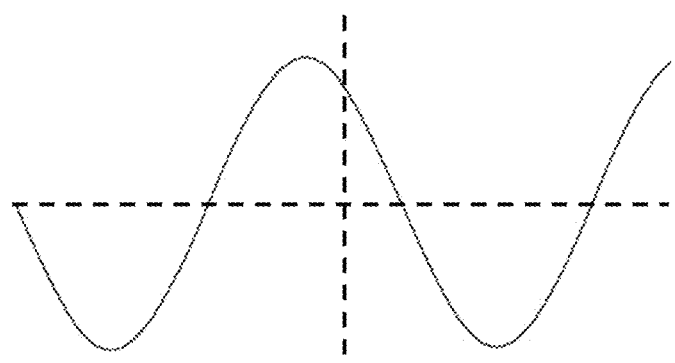
FIGS. 3 and 4 represent, schematically, media modulated by the utilization of the present invention.
Figure 4:
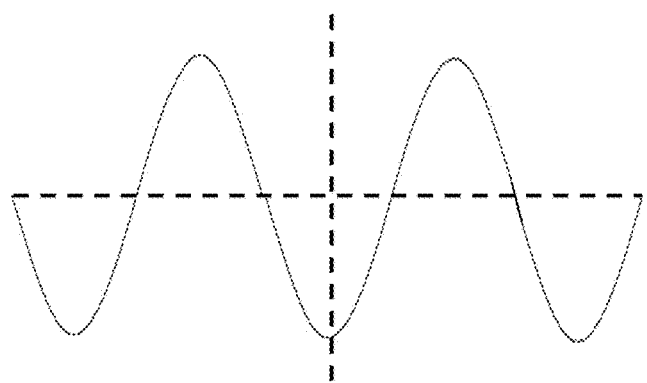

FIGS. 3 and 4, in particular, show a sine-wave signal corresponding to a sound emitted by an electroacoustic transducer. In FIG. 3 the frequency of this signal corresponds to the position of the contact illustrated in FIG. 1, whereas in FIG. 4 the frequency of the signal corresponds to the position of the contact illustrated in FIG. 2. It can therefore be understood that the shortening of the path connecting the electrode results in a frequency step-up.

In some embodiments, the control means 120 controls the emission of a light signal for which an emission parameter is determined as a function of the value detected.

The term "light signal" refers to any signal produced by a light emission source. Such a light signal is, for example, a signal emitted by a diode, screen or video projector.

In some embodiments, the control means 120 controls the emission of a trigger signal in an audiovisual medium being played.

This trigger signal is, for example, a command to pause, play, increase or decrease the sound volume, or a command normally corresponding to pressing a keyboard key.

In some embodiments, the control means 120 controls the emission of a modulation signal for a medium being played.

The modulation signal is, for example, a signal for the modulation of a sound or visual signal for modifying a play parameter of the medium.

In some embodiments, such as that shown in FIG. 1, the control means 120 is separate from the detector 115 and electrodes 105, 110, the device comprising a means 125 for transmitting a wireless signal representative of the value detected towards the control means.

The transmission means 125 is, for example, an antenna associated to the control means 120 configured to emit and receive wireless signals according to the Bluetooth (registered trademark) standard, according to the IEEE 802.11-standard, aka "Wi-Fi", and more generally using high-frequency transmission technology, for example.

In some embodiments, such as that shown in FIG. 1, the device 100 comprises an independent source of electrical power 130, configured to supply the first electrode 105 with electrical current.

This power source 130 is, for example, a button battery.

In some embodiments, the device 100 also comprises a physiological data sensor, eg a cardiometer. The value of the physiological data measured, eg heart rate, is mathematically combined with the impedance of the skin contact to modulate the generation or delivery of sound and/or light signals.

Figure 5:
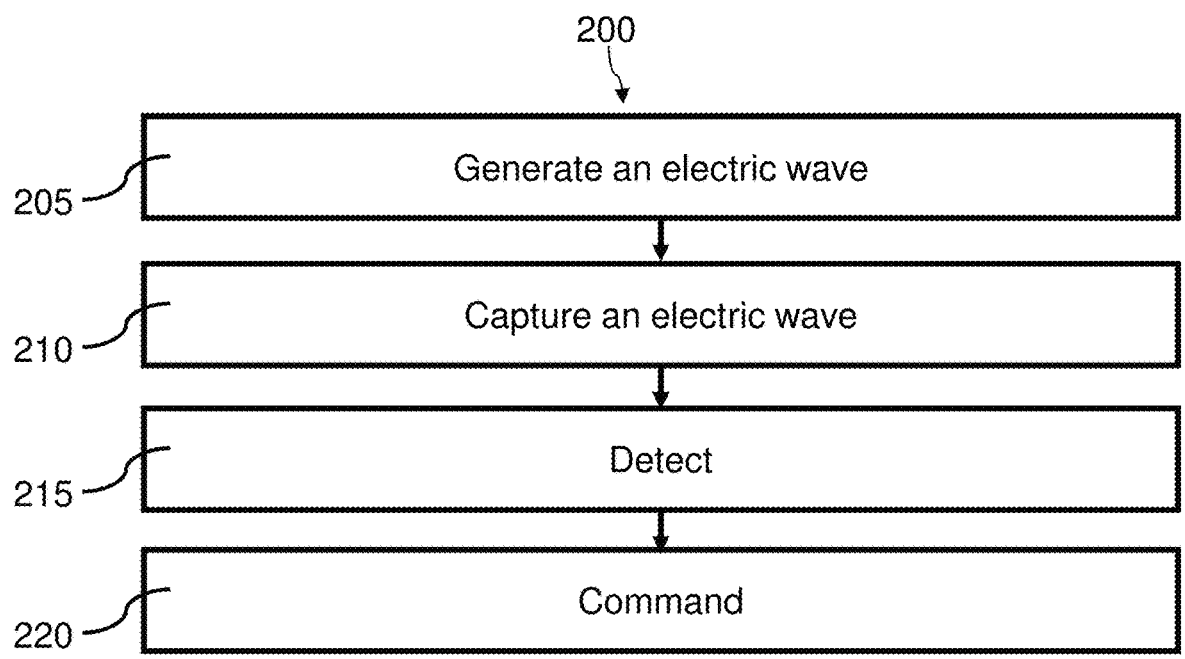
FIG. 5 represents, schematically and in the form of a logical diagram, a particular series of steps of a modulation method.

FIG. 5 shows a particular embodiment of the method 200 enabling the use that is the subject of the present invention. This method 200 of controlling the delivery of a medium comprises:
- a step 205 of generating electric waves transmitted to the skin of a first user by means of a first electrode;
- a step 210 of capturing electric waves transmitted by the skin of a second user by means of a second electrode, where the second user can be the first user;
- a step 215 of detecting the value of an impedance parameter of the junction connecting the electrodes; and
- a control step 220 configured to emit a medium-delivery command according to the value detected.

In some embodiments, during the step 220, the modulation of an audio and/or visual signal also depends on physiological data of at least one user, captured by the device, the device comprising at least one sensor of a user's physiological data. For example, at least one item of physiological data is a heart rate.

This method 200 is implemented, for example, by the use of a device 100 described with reference to FIGS. 1 and 2.

Preferably, the modulation of an audio and/or visual signal comprises the modulation of the frequency of said signal. For example, the sound frequency of a sound or a sonic work is increased when the impedance of the contact decreases. According to another example, the wavelengths emitted by a light source decrease with the impedance of the contact. These variations make the variation effect of the skin contact perceptible.

In some embodiments, the modulation of an audio and/or visual signal comprises the modulation of the rhythm of said signal. For example, the rhythm of a regular beat or the playback rhythm of a sonic work depends on the impedance of the skin contact.

Figure 6:
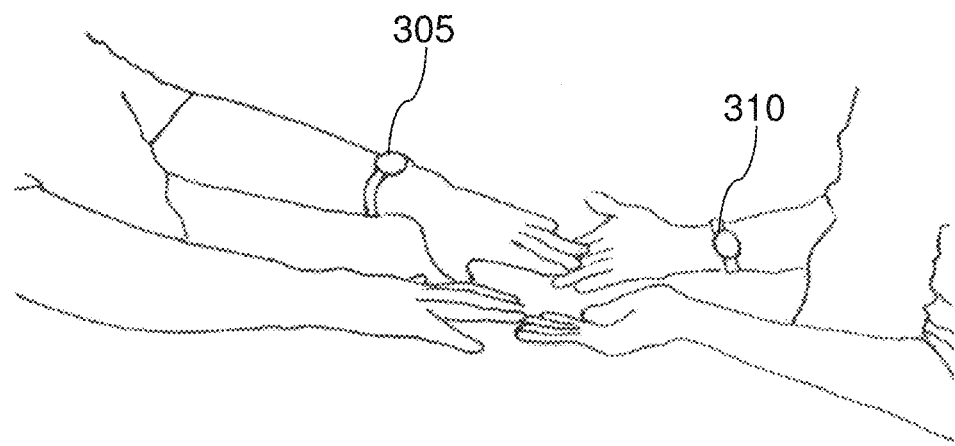
FIG. 6 represents, schematically, a first embodiment of the use that is the subject of the present invention.

FIG. 6 shows, schematically, a first embodiment of the use that is the subject of the present invention, in which each of the two persons, for example a patient and a caregiver, wears a bracelet, respectively 305 and 310, comprising an electrode. Optionally, at least one of the bracelets, preferably associated to the electrode capturing electrical signals, comprises a cardiometer (not shown). Depending on the impedance of the contact between the two users, here represented by a contact between the users' hands, and optionally depending on the heart rate of at least one of the users, the emission of a sound and/or light signal, or an audiovisual signal, is modulated, or the delivery of an audiovisual medium is modulated. In this way, through feedback to at least one of the senses of hearing or sight, each user can sense and control the contact and vary the effects sensed.

Figure 7:
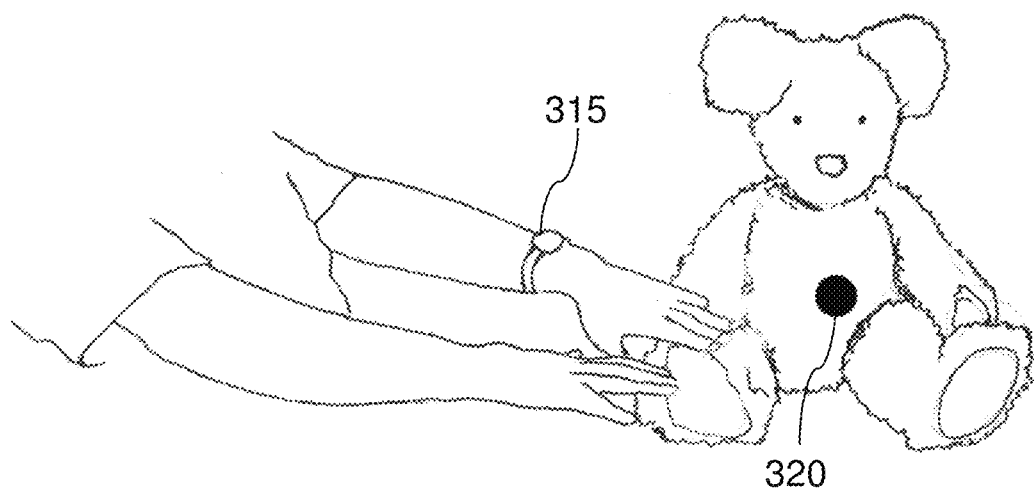
FIG. 7 represents, schematically, a second embodiment of the use that is the subject of the present invention.

FIG. 7 shows a second embodiment of the use that is the subject of the present invention, in which an object, here a bear made of an electrically conductive material, carries an electrode 320. A person, for example a patient, wears a bracelet comprising an electrode 315. Optionally, the bracelet, preferably associated to the electrode capturing electrical signals, comprises a cardiometer (not shown). Depending on the impedance of the contact between the user and the object, and optionally depending on the heart rate of at least one of the users, the emission of a sound and/or light signal, or an audiovisual signal, is modulated, or the delivery of an audiovisual medium is modulated. In this way, through feedback to at least one of the senses of hearing or sight, the user can sense and control the contact and vary the effects sensed.

Therefore, as is understood from reading the description of FIGS. 6 and 7, in some embodiments, the modulation of an audio and/or visual signal also depends on physiological data of at least one user, captured by the device, the device comprising at least one sensor of a user's physiological data. For example, at least one item of physiological data is a heart rate.

Figure 8:
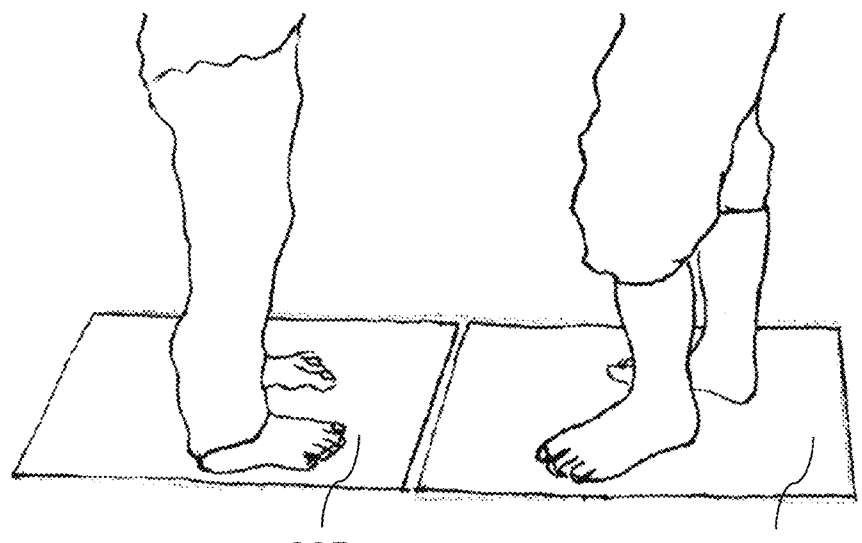
FIG. 8 represents, schematically, a third embodiment of the use that is the subject of the present invention.

FIG. 8 shows, schematically, a third embodiment of the use that is the subject of the present invention, in which two users have their bare feet on two panels 325 and 330, each equipped with an electrode. Depending on the impedance of the contact between two users, for example a contact between the arms or hands of the users, the emission of a sound and/or light signal, or an audiovisual signal, is modulated, or the delivery of an audiovisual medium is modulated. In this way, through feedback to at least one of the senses of hearing or sight, each user can sense and control the contact and vary the effects sensed.

Figure 9:
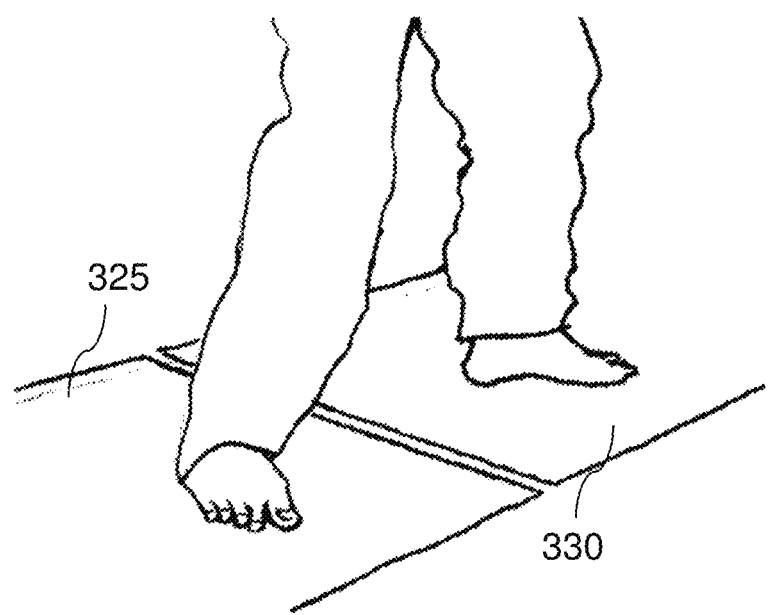
FIG. 9 represents, schematically, a fourth embodiment of the use that is the subject of the present invention.

FIG. 9 shows, schematically, a fourth embodiment of the use that is the subject of the present invention, in which a user places his bare feet on panels 325 and 330.

Figure 10:
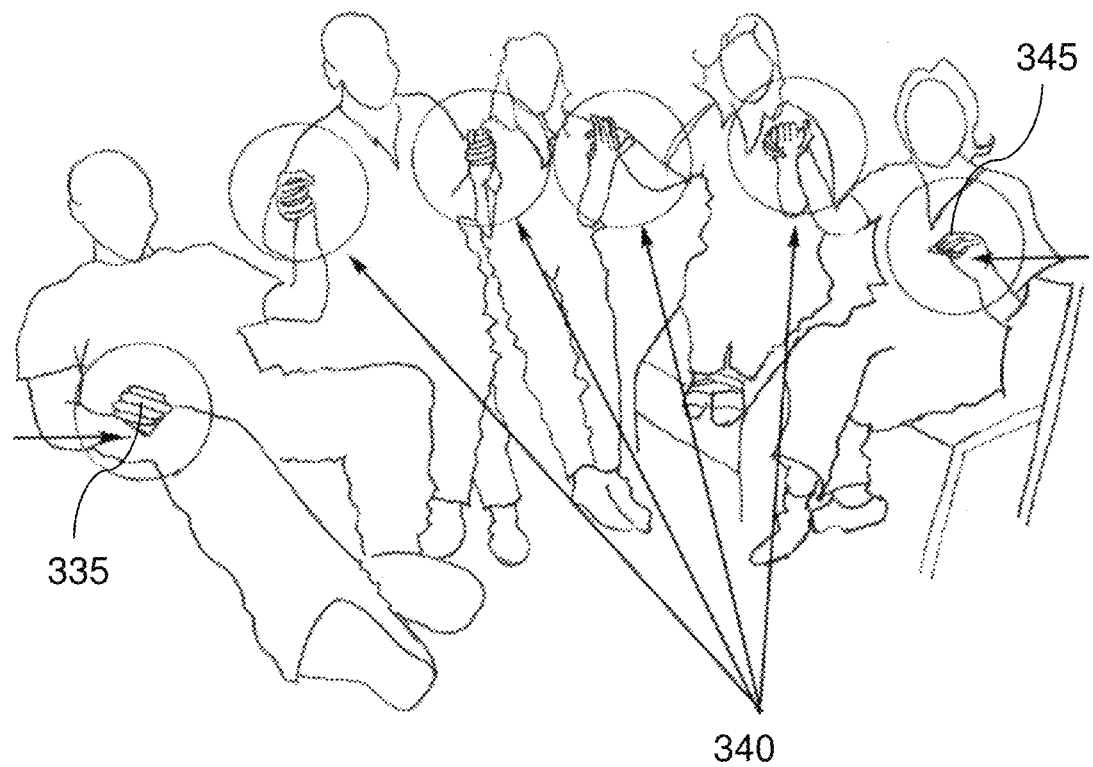
FIG. 10 represents, schematically, a fifth embodiment of the use that is the subject of the present invention.

FIG. 10 shows, schematically, a fifth embodiment of the use that is the subject of the present invention, in which two users are each equipped with an electrode, respectively 335 and 345, for example by means of a bracelet. The areas of contact 340 between two successive users in a chain of users, here five, influences the total impedance between the electrodes 335 and 345.

Figure 11:
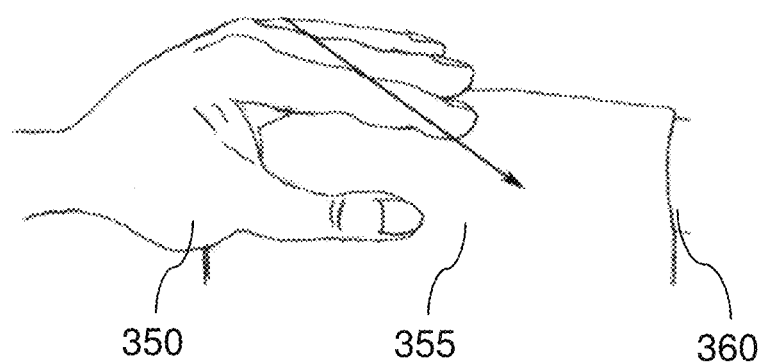
FIG. 11 represents, schematically, a sixth embodiment of the use that is the subject of the present invention.

FIG. 11 shows, schematically, a sixth embodiment of the use that is the subject of the present invention, in which a fabric 355 is placed between the hands 350 and 360 of two users. This fabric, drier or moister, reduces or increases the impedance of the contact between the hands. It is noted that the hands in question can be those of a single user or of two different users.

Figure 12:
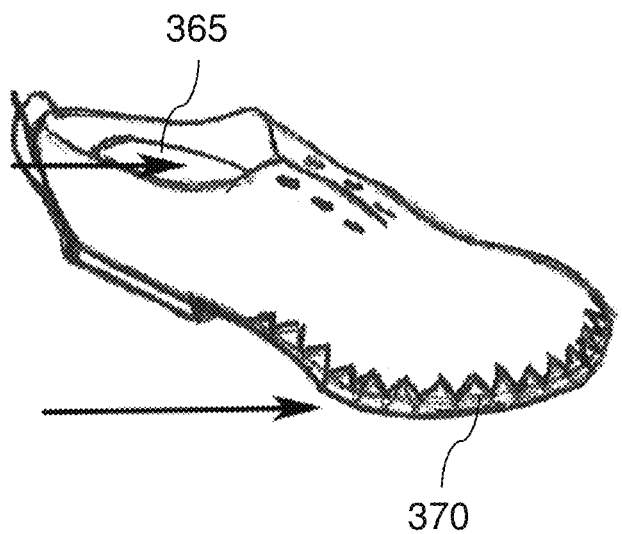
FIG. 12 represents, schematically, a seventh embodiment of the use that is the subject of the present invention.

FIG. 12 shows, schematically, a seventh embodiment of the use that is the subject of the present invention, in which an electrically insulating shoe comprises an internal electrode 365 and an external electrode 370. The electrical contact made by the rest of the body, for example in contact with a tree or a floor, thus forming a conductive circuit between the electrodes, modulates the impedance of the contact with the body of the user.

In each of these embodiments, the modulation of an audio and/or visual signal by a variation in the impedance of at least one contact with the skin of at least one user is used to maintain and/or develop the user's physical and/or mental abilities, by utilizing a device as described with reference to FIGS. 1 to 4.

The invention claimed is:

1. A device of modulation of an audio and/or visual signal by a variation in an impedance of at least one first contact on a skin of a first user to maintain and/or develop the first user's physical and/or mental abilities, said device comprising:
   a first skin electrode configured to generate electric waves, positioned on the first contact with the skin of the first user;
   a second skin electrode configured to capture electric waves, positioned on a second contact with a skin of a second user, wherein the first user and the second user are two different users;
   a detector for detecting a value of an impedance parameter of a junction connecting the electrodes and passing through the first contact and the second contact on the skins of each user;
   a controller configured to transmit a medium-delivery command including a command of modulation of an audio and/or visual signal, wherein the medium-delivery command depends on the value detected; and
   a player configured to receive the command and to play the medium with the modulation of the played medium audio and/or visual signal, according to the command;
   wherein the junction of which the impedance parameter is detected comprises at least one contact between the two different users.

2. The device according to claim 1, wherein the command of modulation of an audio and/or visual signal comprises a command of modulation of a frequency of said signal.

3. The device according to claim 1 wherein the command of modulation of an audio and/or visual signal comprises a command of the modulation of rhythm of said signal.

4. The device according to claim 1, wherein the impedance parameter detected is the resistivity of the junction.

5. The device according to claim 1, wherein the controller is separate from the detector and from electrodes, the device comprising a transmitter configured to transmit a wireless signal representative of the value detected towards the controller.

6. The device according to claim 1, wherein the device comprises an independent source of electrical power, configured to supply the first electrode with electrical current.

7. The device according to claim 1, wherein the device comprises a bracelet comprising the first electrode.

8. The device according to claim 1, wherein the device comprises a plurality of first and/or second electrodes.

9. The device according to claim 1, wherein the controller is configured to command an emission of a sound signal for which an emission parameter is determined as a function of the value detected.

10. The device according to claim 1, wherein the controller is configured to command an emission of a light signal for which an emission parameter is determined as a function of the value detected.

11. The device according to claim 1, wherein the controller is configured to command an emission of a trigger signal in an audiovisual medium being played.

12. The device according to claim 1, wherein the controller is configured to command an emission of a modulation signal for a medium being played.

13. The device according to claim 1, wherein at least one electrode is carried by a panel on which the first user places at least one part of his body.

14. The device according to claim 1, further comprising a sensor of physiological data of at least one user, wherein the controller is configured to command the modulation of an audio and/or visual signal further depending on physiological data of at least one user.

15. The device according to claim 14, wherein at least one item of physiological data sensed by the sensor is an heart rate.

* * * * *